(12) United States Patent
Parodi

(10) Patent No.: US 6,336,933 B1
(45) Date of Patent: Jan. 8, 2002

(54) ENDOVASCULAR DEVICE FOR APPLICATION OF PROSTHESIS WITH SUTURES

(75) Inventor: Juan C. Parodi, Blanco Encalada 1543, C1428 DCO, Buenos Aires (AR)

(73) Assignee: Juan C. Parodi, Blano Encalada (AR)

( * ) Notice: Subject to any disclaimer, the term of this patent is extended or adjusted under 35 U.S.C. 154(b) by 0 days.

(21) Appl. No.: 09/640,554

(22) Filed: Aug. 18, 2000

Related U.S. Application Data

(63) Continuation of application No. 09/266,200, filed on Mar. 10, 1999, now abandoned.

(30) Foreign Application Priority Data

Mar. 13, 1998 (AR) ..................................... P19980101145

(51) Int. Cl.⁷ .............................................. A61B 17/10
(52) U.S. Cl. ....................................................... 606/139
(58) Field of Search ................................. 606/104, 198, 606/108, 139, 144, 148; 604/104, 105, 106, 107

(56) References Cited

U.S. PATENT DOCUMENTS

| | | |
|---|---|---|
| 3,686,740 A | 8/1972 | Shiley |
| 3,799,172 A | 3/1974 | Szpur |
| 4,307,722 A | 12/1981 | Evans |
| 4,781,682 A | 11/1988 | Patel |
| 4,921,484 A | 5/1990 | Hillstead |
| 5,042,707 A | 8/1991 | Taheri |
| 5,330,490 A | 7/1994 | Wilk et al. |
| 5,330,503 A | 7/1994 | Yoon |
| 5,582,616 A | 12/1996 | Bolduc et al. |
| 5,662,700 A | 9/1997 | Lazarus |
| 5,676,697 A | 10/1997 | McDonald |
| 5,702,365 A | 12/1997 | King |
| 5,713,907 A * | 2/1998 | Hogendijk et al. .......... 606/108 |
| 5,855,565 A * | 1/1999 | Bar-Cohen et al. .......... 606/104 |
| 5,980,548 A | 11/1999 | Evans et al. |

FOREIGN PATENT DOCUMENTS

| | | |
|---|---|---|
| EP | 0321912 | 6/1989 |
| EP | 0663184 | 7/1995 |
| WO | WO 9703616 | 6/1997 |
| WO | WO 9953845 | 10/1999 |

\* cited by examiner

Primary Examiner—Paul J. Hirsch
Assistant Examiner—Eduardo C. Robert

(57) ABSTRACT

An endovascular surgical device is disclosed for attaching an endovascular prosthesis to a vascular wall. The device includes a tubular member and an applicator device. The tubular member has longitudinal bands separated by slots that are configured to expand upon being placed in compression. The applicator device has a distal end with a rotary head for applying sutures. A portion of the suture is at least partially positioned in the rotary head. A method is described that includes positioning a prosthesis and an endovascular device within a portion of vascular wall that requires reinforcing or repairing. The tubular part is expanded, forcing the prosthesis and vascular wall to expand. The applicator device applies the suture to attach the prosthesis to the vascular wall. Additional sutures can be applied by removing the applicator device, attaching a second suture and repositioning the applicator device to attach a second suture.

11 Claims, 1 Drawing Sheet

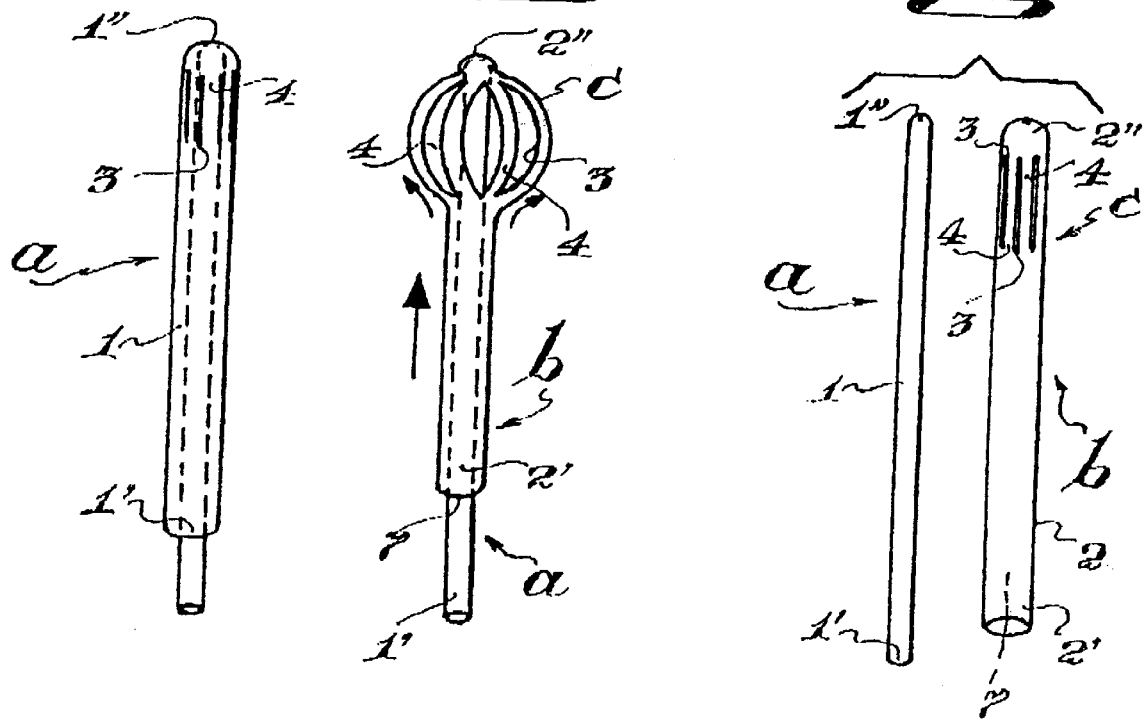
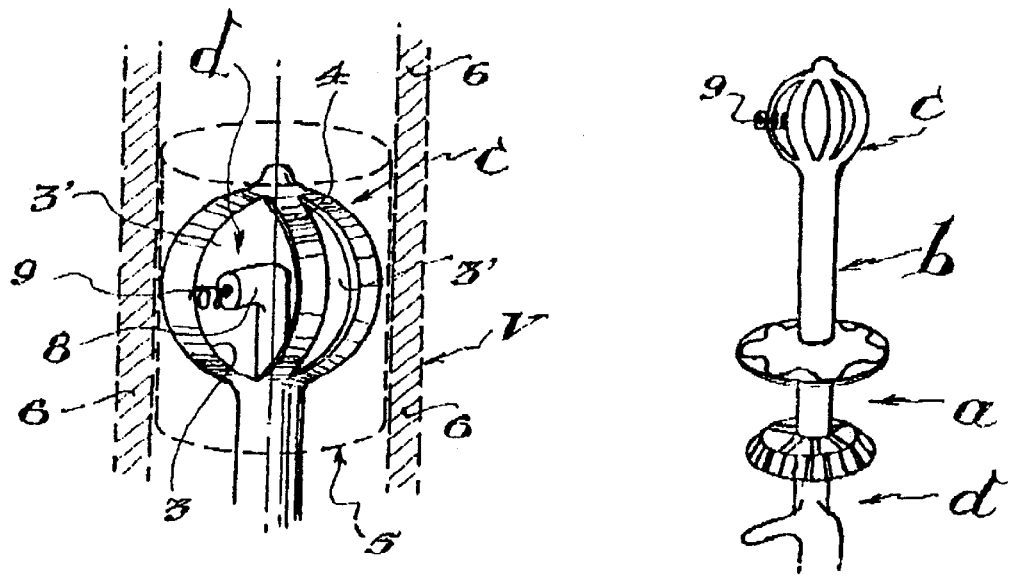

ENDOVASCULAR DEVICE FOR APPLICATION OF PROSTHESIS WITH SUTURES

CROSS REFERENCE TO RELATED APPLICATION

This application is a continuation of U.S. patent application Serial No. 09/266,200, filed Mar. 10, 1999, now abandoned.

BACKGROUND

1. Technical Field

This invention consists of an endovascular device for application of prostheses with sutures that permit maintenance of prosthetic expansion against vascular walls while the holding sutures are applied.

2. Description of Related Art

In pathologies affecting vascular channels, there are currently many common endovascular treatments based on the application of expandable prostheses that, like linings, allow damaged or weakened vascular walls to be supported.

SUMMARY

Both vascular dilations subsequent to treatment and periprosthetic losses create severe problems that are difficult to solve. Recourse is had to internal sutures permitting good attachment of the prostheses for this.

These sutures consist of metal spirals provided with a sharp penetrating end and an anchoring end that are applied by means of devices equipped with rotary applicator heads. In this manner, the above-mentioned spirals pass through the walls of the prosthesis first, and then the vascular walls, achieving a very firm union by means of which the sutured prosthesis conveniently accompanies the dilation of the vascular channel.

However, the devices normally used for this type of treatment do not totally eliminate the risk of the above-mentioned periprosthetic losses or small imperfections in the union between prosthesis and vascular wall.

This is due to the fact that the prosthesis is expanded and the sutures applied in two stages. In the first stage, an inflatable balloon is generally used to expand the prosthesis against the vascular wall. Said balloon is then withdrawn and the spiral suture applicator is then introduced. It is precisely in the period between the withdrawal of the balloon and the application of the sutures that maladjustments can occur, causing serious consequences.

These problems are solved by means of this endovascular device that comprises a support cable on which a tubular piece is mounted in a sliding manner, both connected at their respective distal ends. The tubular part has a number of longitudinal cuts that, in addition to forming circumstantial passages for the suture applicator, make up an expandable e that is simultaneously applicable to the endovascular prosthesis, keeping it expanded against the vascular walls to which it is to be applied.

In this manner, the expandable segment is the tubular part not only expands the prosthesis, it also keeps it expanded while the applicator head applies the spiral sutures through the passages created by the longitudinal cuts.

Moreover, compared to some devices equipped with more complex and costly means of actuation, the simplicity of the mechanism of actuation of this device must be noted.

In effect, its operation is based on the sliding assembly of the tubular part on the support cable, as well as the distal connection between the two parts. This arrangement, by means of the simple actuation of a pushing end, allows the resistance of the folded expanding bands to be overcome such that they unfold outward until the expansion of the segment is achieved.

It is therefore a device that is simple to operate and simple in construction, which has a favorable impact on manufacturing costs.

Illustration

For greater clarity and better comprehension of the subject of the invention, it is illustrated with various figures showing one of its preferred methods of embodiment, all as a simple illustrative and not limitative example:

FIG. 1a is a perspective view of this device in its normally contracted position.

FIG. 1b is a perspective view showing the device in its operating position, with the expandable segment in its position of maximum expansion.

FIG. 2 is a cross-section showing separately the general layout of the support cable and the tubular part.

FIG. 3 is a perspective view showing how the expansion of the expandable segment compresses the expandable prosthesis against the damaged vascular walls. At the same time, it shows how the longitudinal cuts form passages through which the applicator head applies the spiral sutures.

FIG. 4 is a perspective view showing the general layout of this device.

In the various figures, the same reference numbers indicate the same or corresponding parts, and the sets of various components are indicated by letters.

DETAILED DESCRIPTION OF PREFERRED EMBODIMENTS

LIST OF THE MAIN REFERENCES (a) support cable
(b) tubular part
(c) expandable segment of tubular part (b)
(d) suture applicator
(v) vascular channel for application
(1) long body of support cable (a)
(1') proximal end for operative use
(1") distal end for connection
(2) tubular walls of part (b)
(2') proximal pushing end
(2") distal head end
(3) dilatable longitudinal cuts in expandable segment (c)
(3') passages shaped by longitudinal cuts (3)
(4) expander belts on expandable segment (c)
(5) expandable endovascular prosthesis
(6) injured vascular walls of vascular channel (v)
(7) tubular access passage
(8) rotary head of applicator device (d)
(9) spiral sutures applicable by means of rotary head (8)

For the purposes specified, this endovascular device for the application of prostheses (5) with sutures forming the access route for an applicator (d) of sutures (9) of the type with a rotary applicator head (8) for spiral sutures (9) can be introduced endoluminally into vascular channel (v) to which they are to be applied, the walls (6) of which present an injury to which expandable endovascular prosthesis (5) can be applied; said endovascular device is characterized in that it comprises:

a) support cable (a) terminating, at the one end, in a distal connection end (1") and, on the opposite end, in a proximal end for operative use (1');

b) a tubular part (b) that, once mounted in a slidable manner on said support cable (a), has a distal head end (2") connected with said distal connection end (1") of above-cited support cable (1) and, at the opposite end, with proximal pushing end (2'); and c) proximal to distal head end (2") of said tubular part (b), expandable segment (c) formed of a number of dilatable longitudinal cuts (3) that, shaping circumstantial passages (3') for said applicator head (8), define a number of expander belts (4) foldable toward the exterior, as an expansion means for said prosthesis (5).

This invention consists of an endovascular device for application of prostheses with sutures that, in general terms, comprises a support cable (a) on which there is mounted, in a slidable manner, tubular part (b), both (a) and (b) connected by their respective distal ends (1") (2"); said tubular part (b) has a number of longitudinal cuts (3) that, in addition to forming circumstantial passages (3') for an applicator (d) of sutures (d), also compose expandable segment (c) applicable to endovascular prosthesis (5) expandable against vascular walls (6) for the application.

In greater detail, this endovascular device is composed of support cable (a) that consists of semi-flexible long body (1) that, on the one end, terminates in proximal end for operative use (1'), while the opposite end terminates in distal connection end (1").

On this support cable (a), there is mounted tubular part (b) that ends in distal head end (2"). This distal head end (2") is connected to distal connection end (1") of support cable (a). At the opposite end, tubular part (b) terminates in proximal pushing end (2').

Adjacent to above-cited distal head end (2"), tubular part (b) has expandable segment (c) in which its tubular walls (2) are affected by a number of dilatable longitudinal cuts (3). Said longitudinal cuts (3) delimit longitudinal portions of the tubular walls (2) that form expander belts (4) that can be folded toward the exterior.

In this manner, expandable segment (c) has an expansion capacity between two end positions: a normal, contracted position; and another, operating position in which expander belts (4) are folded outward and longitudinal cuts (3) dilated. In this operating position, folded expander belts (4) constitute prosthetic expansion means (5), while dilated longitudinal cuts (3) form passages (3') for an applicator head (8) for spiral sutures (9). Applicator head (8), in turns, forms part of applicator device (d) for spiral sutures (9) that accesses passages (3') of expandable segment (c) through tubular passage (7) made up of tubular walls (2).

In a preferred method of embodiment, expandable segment (c) of tubular part (b) is structured of a semi-flexible material, such that the above-cited expander belts (4) can be folded toward the exterior and retracted.

Furthermore, since support cable (a) and tubular part (b) are joined at their respective distal ends (1") (2"), proximal pushing end (2') of said tubular part (b) is mounted in a sliding manner, guided on long body (1) of above-cited cable (a), thus constituting a means of actuation for expander belts (4) that can be folded toward the exterior.

The Unit Functions in the Following Manner

Once expandable endovascular prosthesis (5) and this device are introduced into the vascular channel for the application (v), same are positioned with regard to damaged vascular walls (6) such that the prosthesis, although not expanded, is interposed between expandable segment (c) and the above-cited vascular walls (6).

Under these conditions, if the operator operates operative end (1') of support cable (a) and, at the same time, presses, in a distal direction, pushing end (2') of tubular part (b), expandable segment (c) of the latter (b) expands. This occurs because, when cable (a) and tubular part (b) are mounted in a sliding manner and connected at their respective distal ends (1")(2"), pressure exerted on pushing end (2') overcomes the resistance of expander belts (4), which fold toward the exterior.

This folding or expansion of expander belts (4) occurs against the internal walls of the prosthesis (5) which is therefore expanded against the damaged vascular walls (6), covering them.

Moreover, the expansion of the above-cited expander belts (4) causes dilation of longitudinal cuts (3) of expandable segment (c). In this manner, the device completes its operating position in that longitudinal cuts (3) achieve their maximum dilation, forming passages (3') through which rotary head (8) of applicator device (d) for spiral sutures (9) appears. These spirals (9) first pass through the walls of prosthesis (5) and then vascular walls (6), producing the permanent attachment of prosthesis (5) in vascular channel (v).

It is indubitable that, once this device is used in practice, changes can be made in certain design and form details without escaping from the fundamental principles substantiated clearly in the following claims.

Having thus specially described and determined the nature of this invention, and since it can be put into use, the following is claimed as exclusive right and property:

1. An endovascular device for suturing a prosthesis to a vascular wall comprising:

a tubular part having a distal end and a proximal end that define a longitudinal axis;

a plurality of longitudinally aligned belt segments defining slots positioned near the distal end of the tubular part, the belt segments being configured to be expandable and retractable;

a support cable including a proximal end and a distal end that is slidably mounted within the tubular part and connected to the distal end of the tubular part;

an applicator device removably positionable within the tubular part, the applicator device having a distal end and a proximal end, wherein the distal end includes a rotary head; and a suture positioned on the rotary head.

2. The endovascular device for suturing a prosthesis of claim 1, wherein the distal end of the applicator device includes a portion that is approximately orthogonal to the longitudinal axis.

3. The endovascular device for suturing a prosthesis of claim 1, wherein the belts of the tubular part are configured to expand outward when the tubular part is placed in compression.

4. The endovascular device for suturing a prosthesis of claim 1, wherein the suture has a spiral shape with a sharp penetrating end and an anchoring end.

5. An endovascular device for suturing, a prosthesis to a vascular wall comprising:

a tubular part having a distal end and a proximal end that define a longitudinal axis, the distal end including a plurality of longitudinally aligned bands defining slots, the bands extending proximally and being configured to be expandable and retractable;

a support cable including a proximal end and a distal end that is slidably mounted within the tubular part and connected to the distal end of the tubular part; and an applicator device removably positionable within the tubular member, the applicator device having a distal end and a proximal end, wherein at least a portion of a suture is configured to be positioned in the distal end, the suture being suitable for connecting an endovascular prosthesis to a vascular wall.

6. The endovascular device for suturing the prosthesis of claim 5, wherein the distal end of the applicator device includes a rotary head portion that is approximately orthogonal to the longitudinal axis, the orthogonal portion being of sufficient length to extend into the area of the slots between the expanded belts to place a suture into the endovascular prosthesis and the vascular wall expanded by the bands.

7. The endovascular device for suturing the prosthesis of claim 5, wherein the tubular part contains a pushing end.

8. The endovascular device for suturing the prosthesis of claim 5, wherein the suture has a spiral shape with a sharp penetrating end and an anchoring end.

9. A method for suturing a prosthesis to a vascular wall comprising the steps of:

providing an endovascular device for fastening a prosthesis to a vascular wall of a patient, the device including a tubular part, a support cable, a suture, and an applicator device, the tubular part containing a distal end portion and a proximal end portion, the distal end portion having longitudinally aligned expandable and retractable bands separated by slots;

positioning the endovascular device and endovascular prosthesis in a first position to support a portion of the vascular wall;

placing the tubular part in a second position wherein the bands have expanded outward;

placing the applicator device with a rotary head in the distal end of tubular part where the bands have expanded outward and applying the suture using the rotary head to attach the prosthesis to the vascular wall;

removing the applicator device and repositioning the applicator device with a second suture positioned on the rotary head attach the prosthesis to the vascular wall; and placing the tubular part in a first position and withdrawing the endovascular device from the patient.

10. The method of claim 9 for suturing a prosthesis to a vascular wall, wherein the step of placing the tubular part in a second position further comprises:

holding the support cable in position while applying a force on a pushing end of the tubular part that places the tubular part under compression and expands the bands;

11. The method of claim 9 for suturing a prosthesis to a vascular wall, wherein the step of applying the suture further comprises:

forwarding the suture until it is anchored into the prosthesis and the vascular wall.

* * * * *